(12) United States Patent
Massen

(10) Patent No.: US 7,209,586 B2
(45) Date of Patent: Apr. 24, 2007

(54) METHOD AND ARRANGEMENT FOR DETECTING THE SPATIAL FORM OF AN OBJECT

(75) Inventor: Robert Massen, Ohningen-Wangen (DE)

(73) Assignee: corpus.e AG, Stuttgart (DE)

( * ) Notice: Subject to any disclaimer, the term of this patent is extended or adjusted under 35 U.S.C. 154(b) by 758 days.

(21) Appl. No.: 10/333,078

(22) PCT Filed: Jul. 17, 2001

(86) PCT No.: PCT/EP01/08241

§ 371 (c)(1),
(2), (4) Date: Jan. 16, 2003

(87) PCT Pub. No.: WO02/06768

PCT Pub. Date: Jan. 24, 2002

(65) Prior Publication Data

US 2003/0142863 A1    Jul. 31, 2003

(30) Foreign Application Priority Data

Jul. 19, 2000  (DE) ................. 100 33 828

(51) Int. Cl.
*G06K 9/00* (2006.01)
(52) U.S. Cl. .................... 382/154; 702/153
(58) Field of Classification Search ........ 382/154; 702/153

See application file for complete search history.

(56) References Cited

U.S. PATENT DOCUMENTS

| | | | | |
|---|---|---|---|---|
| 4,598,420 A | * | 7/1986 | Harvey | 382/152 |
| 5,457,325 A | * | 10/1995 | Huberty | 250/559.29 |
| 5,911,126 A | * | 6/1999 | Massen | 702/153 |
| 5,956,525 A | * | 9/1999 | Minsky | 396/3 |
| 6,383,148 B1 | * | 5/2002 | Pusch et al. | 600/587 |
| 6,546,356 B1 | * | 4/2003 | Genest | 702/153 |
| 6,724,930 B1 | * | 4/2004 | Kosaka et al. | 382/154 |

FOREIGN PATENT DOCUMENTS

| | | |
|---|---|---|
| EP | 0 760 622 B1 | 11/1998 |
| WO | WO 93/02336 | 2/1993 |
| WO | WO 97/14932 | 4/1997 |

OTHER PUBLICATIONS

Niem, Wolfgang; Wingbermuhle, Jochen. Automatic Reconstruction of 3D Objects Using a Mobile Monoscopic Camera. IEEE 1997.*
Webster's II New Riverside University Dictionary. Houghton Mifflin Company, 1994.*

* cited by examiner

*Primary Examiner*—Bhavesh M Mehta
*Assistant Examiner*—John Strege
(74) *Attorney, Agent, or Firm*—Stuart J. Friedman

(57) ABSTRACT

The invention relates to a method of detecting the 3D shape of objects, in which the object is pressed into a plastically deformable mass provided with markers adapted to be evaluated photogrammetrically. After removal of the object from the marked mass, a plurality of photogrammetric images are taken from different views, and the images are evaluated photogrammetrically, the 3D shape of the object being calculated using an association of the markers corresponding in the images. The invention further relates to a corresponding arrangement for carrying out the method and is particularly suited for the detection of the 3D shape of objects whose 3D shape changes under load. One example of this would be the measurement of human feet.

24 Claims, 3 Drawing Sheets

METHOD AND ARRANGEMENT FOR DETECTING THE SPATIAL FORM OF AN OBJECT

Figure 1:
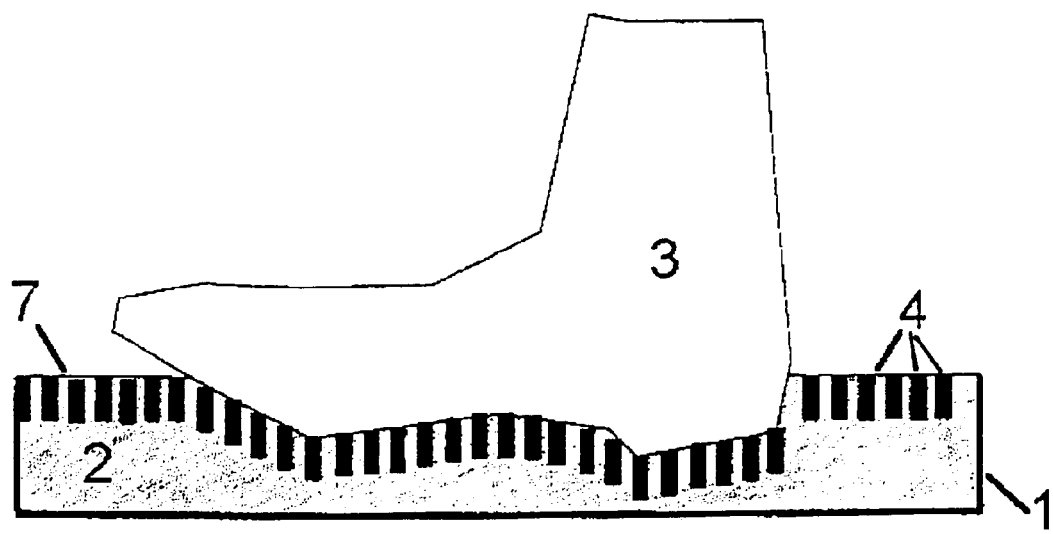

The invention relates to a method and an arrangement for the detection of the 3D shape of an object such as a human foot.

Detection of the three-dimensional shape (3D shape) of bodies and body parts is an important preliminary stage for the production and selection of products whose shape needs to be adapted to the shape of the bodies or body parts. Examples of such products are shoes, footbeds or arch supports, prostheses, ortheses, or articles of clothing.

It is known to detect body parts, e.g., optically, using laser triangulation methods, methods based on stripe projection, or by optical detection of a sequence of silhouette outlines. In contrast to these methods, which are relatively involved because of their mechanically and optically accurately constructed and calibrated systems, European Patent EP 0 760 622, "Sensing Process and Arrangement for the Three-Dimensional Shape in Space of Bodies or Body Parts", discloses a very simple solution which is based on the photogrammetric evaluation of images of the body part which are obtained from non-calibrated imaging positions. To this end, the body part is clad in an elastic envelope provided with markers adapted to be evaluated photogrammetrically.

German Patent Application No. 100 25 922.7 "Automatische photogrammetrische Digitalisierung von Körpern und Objekten" (Automatic photogrammetric digitization of bodies and objects) further discloses how by a special marking of the background of such markers, i.e. by applying area markers, a referencing of the markers (point markers), i.e. an association of pairs of identical point markers in the different overlapping images can be facilitated and automated.

All of these aforementioned processes digitize the body when unloaded. In particular in the case of soft tissue, however, the 3D shape of a loaded body differs greatly from the 3D shape of an unloaded body.

For numerous products intended to be adapted to the body, such as a footbed, a seat shaped to fit a person's anatomy, etc., the spatial coordinates of the body part deformed under load are required rather than those of the unloaded and non-deformed body part.

When measuring the sole of the foot for manufacturing a fitting insole or arch support or a footbed made to fit, for example, the conventional procedure involves the person placing the foot into a plastically deformable mass, and obtaining an impression from this deformed mass using traditional molding techniques, such impression constituting the starting position for preparing the arch support. This is an awkward, lengthy and costly process which could be considerably improved by an automatic digitization of the sole of the foot under load.

It is therefore the object of the invention to provide a simple method and a simple arrangement for the detection of the 3D shape of an object, which solve the problems explained above appearing in previous methods and arrangements and which are more particularly suitable for simple detection of the 3D shape of objects that need to be measured under load.

This object is attained by a method of detecting the 3D shape of an object, wherein a plastically deformable mass is provided which has at least one surface portion provided with markers adapted to be evaluated photogrammetrically, the object is impressed on the surface portion into the mass such that the mass deforms corresponding to the 3D shape of the object, the object is removed from the deformed mass, a plurality of images are taken of the deformed mass provided with the markers from respective different views, and the 3D shape of the object is determined from the images by means of a photogrammetric process.

The object is further attained by an arrangement for detecting the 3D shape of an object by photogrammetry, comprising an imaging system for obtaining photogrammetric images and a system for photogrammetrically evaluating the images and for determining the 3D shape, which is characterized in that it further comprises a plastically deformable mass which has at least one surface portion provided with markers adapted to be evaluated photogrammetrically.

In accordance with the invention the optical detection of the 3D shape of an impression material loaded and deformed by a body part is achieved in that the deformable impression material is characterized by high-contrast markers adapted to be evaluated photogranunetrically. In particular, in accordance with the invention these markings may consist of inclusions whose color differs from the color of the deformable impression mass or of differently colored local colorations of the impression material. By detecting a series of overlapping two-dimensional images (2D images) from unknown imaging positions of the deformed and marked impression mass, the three-dimensional shape (3D shape) of the impression and, hence, the 3D shape of the body part deformed under load can be determined from these 2D images in a simple way using known methods of photogrammetry.

Advantageous further developments of the invention are characterized in the dependent claims.

Figure 2:
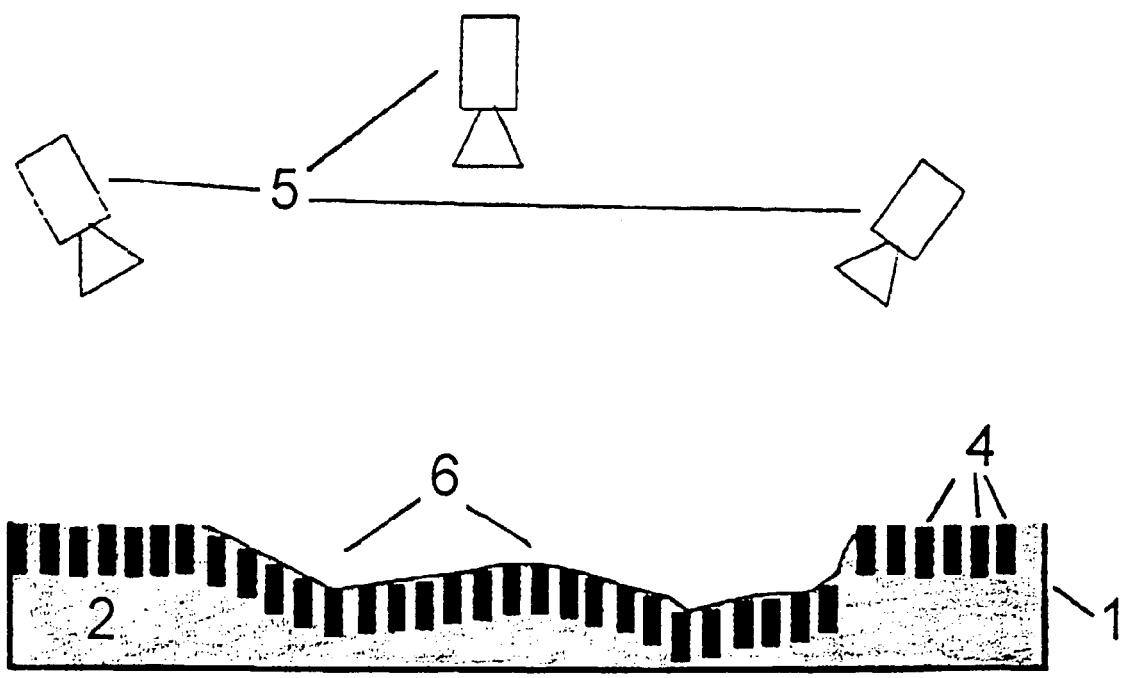
Figure 3:
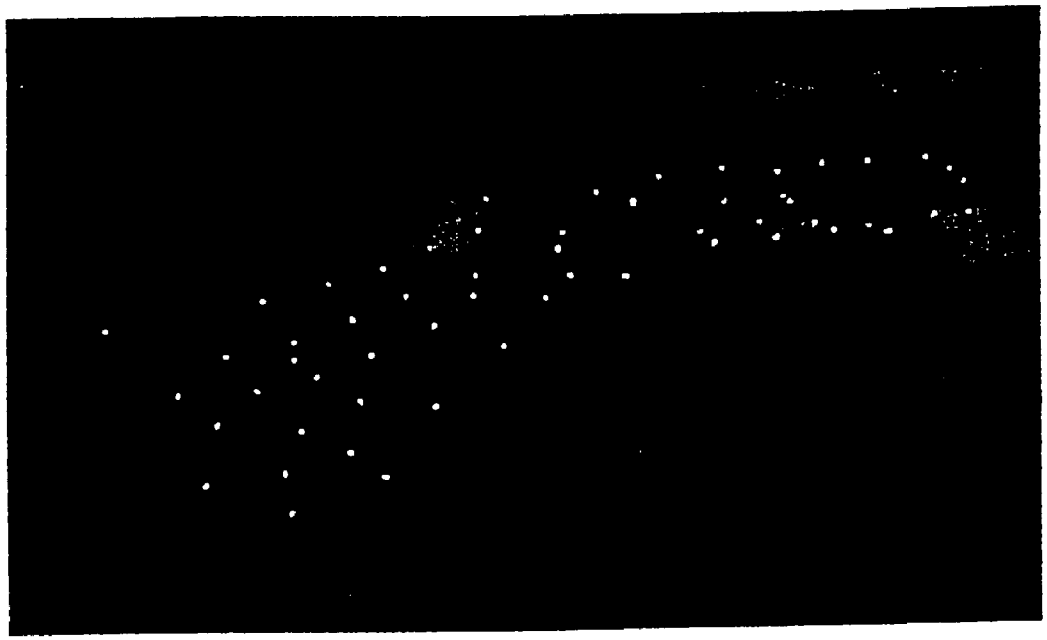

Further features and advantages of the invention will be apparent from the following description of an embodiment with reference to the drawings, in which:

FIG. 1 shows a plastically deformable impression mass used in one embodiment of the invention and provided with markers adapted to be evaluated photogrammetrically, the impression mass being located in an impression frame and being used to prepare an impression of the sole of the foot under load;

FIG. 2 illustrates a schematic arrangement of cameras the positions of which are not known and which are used to take overlapping 2D images of the impression which contain the markers and the positions thereof in relation to the 2D coordinates of these images; and FIG. 3 shows, as an example, a pseudo 3D representation of markers reproducing the three-dimensional shape of the footbed resulting from the impression in FIG. 2.

The method of the invention will now be described by way of example in connection with a typical application, the detection of the sole of a foot under load for manufacturing a footbed that fits anatomically.

This example is, of course, by no means the only possible application of the method in accordance with the invention. For instance, the detection of a 3D impression of the buttocks for manufacturing anatomically adapted seating surfaces would be another example where the detection of the 3D geometry of a body deformed by load is important. Many other applications are conceivable.

Within the scope of the idea of the invention, the terms "object" or "body" are by no means limited to human or animal bodies only, but further cover any physical bodies such as, e.g., mechanical models, antique statues, sculptures or similar three-dimensional spatial shapes.

As shown in FIG. 1, within the frame of a mold 1 there is held a plastically deformable mass 2 into which a person places his/her foot 3 under load. At least a portion 7 of the surface of the mass 2 is provided with markers 4 that are adapted to be evaluated photogrammetrically.

The mass 2 consists of a base material of a single color, into which a number of markers 4 adapted to be evaluated photogrammetrically are let in, whose contrasting color stands out against the color of the base material. These markers may consist of embedded pins of a different color, for example, which are made of the same material as the base material and are let into the base material. The pins may be cylindrical, for example. The base material may consist of commonly available deformable materials, for example, such as plaster, wax, alginate, or elastomers (e.g., silicones).

In a preferred embodiment a plastically deformable material is selected which may be reversibly deformed; after deformation caused by the pressure exerted by the object and after termination of the photogrammetric evaluation of the impression, the material may be returned to its original form under the influence of energy, heat, light, or mechanical energy. Those of ordinary skill in the art are familiar with prior art materials of this type. When such a material is used, the mass provided with photogrammetric markers may be reused as often as desired.

According to the invention, for a simple photogrammetric evaluation the background around these markers may also be marked by zones of a different color. This results in a marking on two levels, namely consisting of point markers and area markers, each of the area markers comprising a plurality of point markers, forming a background of the point markers, and having a characteristic optical configuration.

The impression mass 2 will deform under the load of the foot placed onto the surface portion 7 of the mass 2. The markers 4 which are visible from outside will be shifted accordingly both laterally and in regard to the depth thereof.

After the foot 3 has been removed from the mass 2, images are taken of the impression 6 that is left, illustrated in FIG. 2, from a number of overlapping imaging positions, using an imaging system which may include a camera or, as shown in FIG. 2, a plurality of cameras 5, and a number of 2D images are prepared, in which the markers 4 occupy different XY positions.

A person of ordinary skill in the art of photogrammetry and short-range photogrammetry knows how to evaluate such images for obtaining the 3D coordinates, which is why this will not be explained in greater detail herein.

In the photogrammetric method, first an image processing of the images taken is carried out, in which the markers respectively corresponding in the images are associated with one another. Based on the marker association, the 3D shape of the impression and, from this, the 3D shape of the object is then determined using known mathematical methods of photogrammetry.

Where point and area markers are employed, as set forth above, in the image processing of the images first the area markers respectively corresponding in the images are associated with one another using their characteristic optical configurations. Then the point markers comprised by the area markers and respectively corresponding in the images are associated with one another with the aid of the area marker association. Then, using the point marker association, the 3D shape of the object is determined by means of a photogrammetric evaluation process.

In a preferred embodiment, a measuring rod may be mounted on that side of the mold holding the plastically deformable mass which is opposite to the photogrammetric imaging system, the measuring rod having arranged thereon at least two photogrammetric markers at a known distance from each other. Such a measuring rod may consist, e.g., of a rigid, straight rod or plate having the markers applied thereon. The measuring rod may of course also be arranged separately beside the mold. The photogrammetric images are then taken in such a way that at least two images of the impression bearing the markers are taken from any desired positions, with the measuring rod being also included in the images at the same time. This allows the 3D shape of the impression or of the object impressed to be calculated later in absolute values with the aid of the unit of length given by the measuring rod when the images are evaluated photogrammetrically.

FIG. 3 shows, by way of example, the pseudo 3D representation of the markers reflecting the 3D shape of the footbed and thus permitting an automatic production of a footbed using, e.g., a triaxial cutter.

In accordance with the invention, the impression material may also be marked so as to make it suitable for photogrammetric evaluation in that it is covered, prior to being loaded, by a marked elastic envelope, as described in EP 0 760 622, which may consist of a textile material or a synthetic material, for instance. Preferably, this envelope is intended to adhere to the impression material, so that the deformation of the mass is transferred as accurately as possible to the deformation of the elastic envelope. Use of such an envelope solves the problem of hygiene that is created when there is a direct skin contact with the impression mass.

As a disposable article, this envelope obviates the necessity of a costly disinfection of the impression material following each use.

The method according to the invention may be transferred to many other impression or molding applications, of which only a few will be listed as an example:

a) the manufacture of anatomically fitting seating surfaces by use of a marked, flat, plastic mass into which the customer sits himself down, thus leaving an impression of his buttocks deformed by load;

b) the manufacture of spectacle frames that fit well in the nose area by an impression of the region of the nasal root, using an impression material marked in accordance with the invention;

c) the manufacture of copies of antique objects by producing an impression in a plastic material marked in accordance with the invention.

The terms "detection of the 3D shape of an object" and "determination of the 3D shape of an object" as used in the present specification and in the claims are intended to be construed in a sense so as to include detection of the negative shape of the object, i.e. the impression of an object, since the positive shape of the object also implicitly results therefrom, i.e. as a result, the measurements of the object are provided. These terms are further intended to relate also to the detection of the 3D shape of a part of an object, such as, e.g., of a foot as part of the human body.

The invention claimed is:

1. A method of detecting the 3D shape of an object, wherein a plastically deformable mass is provided which has at least one surface portion provided with markers adapted to be evaluated photogrammetrically, the object is impressed on the surface portion into the mass such that the mass deforms under load of the object and an impression is formed in the deformed mass corresponding to the 3D shape of the object such that the markers are shifted spatially with respect to their positions in the mass prior to deformation and with regard to the depth of the impression, the object is removed from the deformed mass, a plurality of images are taken of the shifted markers provided on the impression formed in the deformed mass from respective different views, and the 3D shape of the object is determined from the images by means of a photogrammetric process.

2. The method as claimed in claim 1, wherein in the photogrammetric process an image processing of the images is performed, in which the markers respectively corresponding in the images are associated with one another, and the 3D shape of the object is determined using the marker association.

3. The method as claimed in claim 1 or 2, wherein the provision of the plastically deformable mass which has at least one surface portion provided with markers adapted to be evaluated photogrammetrically is effected by providing a plastically deformable mass having bodies enclosed therein which have a color that is different from the color of the mass and which are visible from outside in the area of the surface portion.

4. The method as claimed in claim 1 or 2 wherein the provision of the plastically deformable mass which has at least one surface portion provided with markers adapted to be evaluated photogrammetrically is effected by applying markers of a color that is different from the color of the mass onto the surface portion portion of the plastically deformable mass.

5. The method as claimed in claim 1 or 2 wherein the provision of the plastically deformable mass which has at least one surface portion provided with markers adapted to be evaluated photogrammetrically is effected by placing an elastic envelope provided with markers on the surface portion of the plastically deformable mass.

6. The method as claimed in claim 1, wherein the markers consist of point markers and area markers, each of the area markers comprising a plurality of point markers, forming a background of the point markers, and having a characteristic optical configuration.

7. The method as claimed in claim 6, wherein in the image processing of the images first the area markers respectively corresponding in the images are associated with one another using their characteristic optical configurations, and then the point markers comprised by the area markers and respectively corresponding in the images are associated with one another with the aid of the area marker association, and using the point marker association, the 3D shape of the object is determined by means of a photogrammetric evaluation process.

8. The method as claimed in claim 1, wherein the plastically deformable mass is provided in a mold which serves to hold the mass.

9. The method as claimed in claim 1, wherein the object is a body part of a person, whose 3D shape is to be measured under load.

10. The method as claimed in claim 9, wherein the object is a foot.

11. The method as claimed in claim 1, wherein the object is a statue.

12. The method as claimed in claim 1, wherein the plastically deformable mass provided is a reversibly deformable mass which, once the images have been taken, is returned to its original form which it had taken prior to the impression by the object.

13. The method as claimed in claim 12, wherein the reversibly deformable mass is returned to its original form under the influence of energy, heat, light, or mechanical energy.

14. The method as claimed in claim 1, wherein prior to obtaining the images, a measuring rod is arranged beside the surface portion of the deformable mass bearing the markers adapted to be evaluated photogrammetrically, the measuring rod having arranged thereon at least two additional markers which are also adapted to be evaluated photogrammetrically, said additional markers being arranged at a known distance from each other.

15. The method as claimed in claim 14, wherein at least two of the images of the mass provided with markers are taken such that the measuring rod is included in the image taken.

16. An arrangement for detecting the 3D shape of an object by photogrammetry, comprising an imaging system for obtaining photogrammetric images and a system for photogrammetrically evaluating the images and for determining the 3D shape of the object, wherein the arrangement further comprises a plastically deformable mass operable to deform under load of the object such that an impression is formed in the deformed mass corresponding to the 3D shape of the object which has at least one surface portion provided with markers adapted to be evaluated photogrammetrically, said markers being configured to shift spatially with respect to their positions in the mass prior to deformation and with regard to the depth of the impression when the mass deforms under load of the object such that said images are of the shifted markers provided on the impression formed in the deformed mass.

17. The arrangement as claimed in claim 16, wherein bodies of a color different from the color of the mass are provided to serve as markers, the bodies being enclosed in the mass and being visible from outside.

18. The arrangement as claimed in claim 16, wherein color markings serving as markers are provided on the surface portion of the mass and have a color that is different from the color of the mass.

19. The arrangement as claimed in claim 16, wherein an elastic envelope is provided having markers applied thereon, which is pulled over the mass in the area of the surface portion and adheres to the mass.

20. The arrangement as claimed in any of claims 16 to 19, wherein further provided is a mold to hold the mass.

21. The arrangement as claimed in claim 16, wherein the platically deformable mass is a reversibly deformable mass.

22. The arrangement as claimed in claim 21, wherein the reversibly deformable mass is made such that it can be returned to its original form under the influence of energy, heat, light, or mechanical energy.

23. The arrangement as claimed in claim 16, wherein a measuring rod is provided which bears at least two additional markers adapted to be evaluated photogrammetrically, arranged at a known distance from each other, the measuring rod being arranged beside the surface portion of the deformable mass.

24. The arrangement as claimed in claim 23, wherein the measuring rod is connected to the mold holding the mass.

* * * * *